(12) United States Patent
Chancellor et al.

(10) Patent No.: US 8,453,510 B2
(45) Date of Patent: Jun. 4, 2013

(54) ULTRASONIC TRANSDUCER SYSTEM AND EVALUATION METHODS

(75) Inventors: David M. Chancellor, Dewey, OK (US); Gangerico G. Ramos, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 201 days.

(21) Appl. No.: 13/184,184

(22) Filed: Jul. 15, 2011

(65) Prior Publication Data

US 2012/0017685 A1    Jan. 26, 2012

Related U.S. Application Data

(60) Provisional application No. 61/367,186, filed on Jul. 23, 2010.

(51) Int. Cl.
*G01N 29/34* (2006.01)
(52) U.S. Cl.
USPC .................. 73/632; 73/598; 73/600; 73/602
(58) Field of Classification Search
USPC .................. 73/632, 594, 597, 598, 599, 600, 73/602
See application file for complete search history.

(56) References Cited

U.S. PATENT DOCUMENTS

| 5,265,461 | A |  | 11/1993 | Steiger et al. |
|---|---|---|---|---|
| 5,435,187 | A | * | 7/1995 | Ewy et al. ........................ 73/856 |
| 5,767,399 | A |  | 6/1998 | Smith et al. |
| 6,401,523 | B1 | * | 6/2002 | Fernandes et al. ................ 73/38 |
| 6,655,213 | B1 | * | 12/2003 | Reinhardt et al. ............. 73/597 |
| 7,099,810 | B2 |  | 8/2006 | Mandal |
| 7,380,466 | B2 | * | 6/2008 | Deeg .............................. 73/803 |
| 8,082,104 | B2 | * | 12/2011 | de Reynal ........................ 702/9 |

FOREIGN PATENT DOCUMENTS

RU        2342646       2/2007

* cited by examiner

*Primary Examiner* — J M Saint Surin
(74) *Attorney, Agent, or Firm* — ConocoPhillips Company

(57) ABSTRACT

Methods and systems are provided for evaluating rock specimens subjected to high pressures and temperatures by ultrasonic evaluation utilizing various transducer enhancements. Certain embodiments contemplate configuring ultrasonic evaluation systems to provide more accurate measurements, enhanced protection of transducer elements, fewer metal interfaces between transducer elements and test specimens, and easier access to transducer elements for maintenance and replacement. Additionally, certain embodiments allow for sequential or simultaneous p-wave and s-wave measurements of a test specimen. These enhancements translate into a more accurate and efficient ultrasonic evaluation system offering higher resolution measurements.

25 Claims, 3 Drawing Sheets

ULTRASONIC TRANSDUCER SYSTEM AND EVALUATION METHODS

CROSS-REFERENCE TO RELATED APPLICATIONS

This application is a non-provisional application which claims the benefit of and priority to U.S. Provisional Application Ser. No. 61/367,186 filed Jul. 23, 2010, entitled "Ultrasonic Transducer System and Evaluation Methods," which is hereby incorporated by reference in its entirety.

FIELD OF THE INVENTION

The present invention relates generally to methods and systems for ultrasonic evaluation of test specimens. More particularly, but not by way of limitation, embodiments of the present invention include methods and systems for evaluating rock specimens subjected to high pressures and temperatures by ultrasonic evaluation utilizing various transducer enhancements.

BACKGROUND

Ultrasonic Testing (or UT for short) is one form of nondestructive evaluation technique that uses high frequency sound energy to conduct examinations and make measurements of various materials. Ultrasonic inspection can be used for flaw detection/evaluation, dimensional measurements, material characterization, and other property determinations. In the evaluation of formation rocks, it is often desired to measure properties of formation rock specimens under various pressure and temperature conditions, sometimes under fluid flow conditions.

A typical UT inspection system consists of several functional units, such as the pulser/receiver, transducer, and display devices. A pulser/receiver is an electronic device that can produce high voltage electrical pulses. Driven by the pulser, the transducer generates high frequency ultrasonic energy. The sound energy is introduced and propagates through the materials in the form of sound waves. When the wave path encounters a discontinuity (such as a crack), part of the wave energy will be reflected back from the flaw surface. The reflected wave signal is transformed into an electrical signal by the transducer and may be visually displayed, such as on a screen. The reflected signal strength may be displayed versus the time from signal generation to when an echo was received. Signal travel time can be directly related to the distance that the signal travels. From the signal, information about the reflector location, size, orientation, and other features may be determined. With automated systems, detailed images of materials may be produced.

Ultrasonic testing is based on time-varying deformations or vibrations in materials, which is generally referred to as acoustics. All material substances are comprised of atoms, which may be forced into vibrational motion about their equilibrium positions. Many different patterns of vibrational motion exist at the atomic level; however, most are irrelevant to acoustics and ultrasonic testing. Acoustics is focused on particles that contain many atoms that move in unison to produce a mechanical wave. When a material is not stressed in tension or compression beyond its elastic limit, its individual particles perform elastic oscillations. When the particles of a medium are displaced from their equilibrium positions, internal (electrostatic) restoration forces arise. It is these elastic restoring forces between particles, combined with inertia of the particles that leads to the oscillatory motions of the medium.

In solids, sound waves can propagate in four principle modes that are based on the way the particles oscillate. Sound can propagate as longitudinal waves, shear waves, surface waves, and in thin materials as plate waves. Longitudinal and shear waves are the two modes of propagation most widely used in ultrasonic testing.

In longitudinal waves, the oscillations occur in the longitudinal direction or the direction of wave propagation. Since compressional and dilational forces are active in these waves, they are also called pressure or compressional waves. They are also sometimes called density waves because their particle density fluctuates as they move. Compression waves can be generated in liquids, as well as solids, because the energy travels through the atomic structure by a series of compressions and expansion (rarefaction) movements.

In the transverse or shear wave, the particles oscillate at a right angle or transverse to the direction of propagation. Shear waves require an acoustically solid material for effective propagation, and therefore, are not effectively propagated in materials such as liquids or gasses. Shear waves are relatively weak when compared to longitudinal waves. In fact, shear waves are sometimes generated in materials using some of the energy from longitudinal waves.

As mentioned previously, longitudinal and transverse (shear) waves are most often used in ultrasonic inspection. The conversion of electrical pulses to mechanical vibrations and the conversion of returned mechanical vibrations back into electrical energy is the basis for ultrasonic testing. The active element is the heart of the transducer as it converts the electrical energy to acoustic energy, and vice versa. The active element is basically a piece of polarized material (i.e. some parts of the molecule are positively charged, while other parts of the molecule are negatively charged) with electrodes attached to two of its opposite faces. When an electric field is applied across the material, the polarized molecules will align themselves with the electric field, resulting in induced dipoles within the molecular or crystal structure of the material. This alignment of molecules causes the material to change dimensions. This phenomenon is known as electrostriction. In addition, a permanently-polarized material such as quartz ($SiO_2$) or barium titanate ($BaTiO_3$) will produce an electric field when the material changes dimensions as a result of an imposed mechanical force. This phenomenon is known as the piezoelectric effect.

The active element of most acoustic transducers used today is a piezoelectric ceramic, which can be cut in various ways to produce different wave modes. In particular, p-wave piezoelectric ceramic elements generate primarily longitudinal waves, whereas s-wave piezoelectric ceramic generate primarily transverse (shear) waves.

Preceding the advent of piezoelectric ceramics in the early 1950's, piezoelectric crystals made from quartz crystals and magnetostrictive materials were primarily used. When piezoelectric ceramics were introduced, they soon became the dominant material for transducers due to their good piezoelectric properties and their ease of manufacture into a variety of shapes and sizes. Additionally, they operate at low voltage and are usable up to about 300° C. The first piezoceramic in general use was barium titanate, and that was followed during the 1960's by lead zirconate titanate compositions, which are now the most commonly employed ceramic for making transducers. New materials such as piezo-polymers and composites are also being used in some applications.

The thickness of the active element is determined by the desired frequency of the transducer. A thin wafer element vibrates with a wavelength that is twice its thickness. Therefore, piezoelectric crystals are typically cut to a thickness that is ½ the desired radiated wavelength. The higher the frequency of the transducer, the thinner the active element. The primary reason that high frequency contact transducers are not produced is because the element is very thin and too fragile.

Conventional systems for ultrasonic inspection however suffer from a variety of limitations and disadvantages. Many conventional ultrasonic evaluation devices require the surface material of a specimen to be accessible to transmit ultrasound through the specimen. Such devices are problematic for evaluating rock specimens under pressure for a variety of reasons. For one, conventional devices often employ a coupling medium to promote the transfer of sound energy into the test specimen. This coupling medium is often a conductive gel or glue. Unfortunately, this coupling medium breaks down under certain high pressure/temperature conditions resulting in the coupling medium being limited to a narrow range of conditions. In some cases, the coupling medium can only withstand a few pressure cycles before failing, thus substantially complicating their use.

Where rock specimens are tested in a fluid-filled pressure chamber, the crystal or transducer element is often exposed to the pressurized liquid. Exposure of the crystal to this pressurized fluid can adversely affect measurements. Additionally, corrosive liquids can attack the crystals or transducer elements that are mounted on rock specimens. Where crystals are bonded directly on the specimen, accessing a rock specimen or the crystal itself for maintenance, adjustment, or replacement is difficult and cumbersome.

Some conventional ultrasonic transducers employ transducer elements mounted on a platen which then indirectly interfaces with a rock specimen. Some of these conventional devices use springs, rubber, or other flexible materials to press crystals against the surface of the steel platen. These devices are often overly complicated and frustrate access to transducer element. In some cases, crystals are molded in a resin platen. Again, this arrangement makes access and maintenance of the crystals exceedingly difficult.

Conventional ultrasonic measuring devices using the platen arrangement often have multiple metal interfaces between the transducer element and the rock specimen. These multiple metal interfaces introduce additional measurement errors. Moreover, such devices usually result in excessive distance between the transducer element and the rock specimen. Some conventional ultrasonic measuring devices are arranged such that fluid flow is transverse to the axis of ultrasonic measurement, which further complicates ultrasonic measurements and analysis.

Other conventional devices only have one type of transducer element, a p-wave crystal or an s-wave crystal, thus limiting the amount of useful information that may be obtained by such devices. To circumvent this problem, some conventional devices utilize a stacked disk arrangement, for example a p-crystal as a full disk, immediately on top of an S-full-disk. This arrangement, while allowing for measurement of both longitudinal and shear waves suffers from measurement inaccuracies and errors caused by the inducement of vibration in the one of the crystals by the other crystal. Thus, the stacked configuration allows both types of waves to be measured but results in less accurate measurements that are degraded in resolution. Additionally, in the stacked configuration, p- and s-waves cannot be transmitted at the same time further limiting their usefulness.

Accordingly, there is a need in the art for improved ultrasonic measurement systems and methods that address one or more disadvantages of the prior art.

SUMMARY

The present invention relates generally to methods and systems for ultrasonic evaluation of test specimens. More particularly, but not by way of limitation, embodiments of the present invention include methods and systems for evaluating rock specimens subjected to high pressures and temperatures by ultrasonic evaluation utilizing various transducer enhancements.

One example of a system for evaluating a rock specimen by ultrasonic evaluation comprises: a first housing having a first chamber, the first housing having a first axis therethrough; wherein the first chamber is accessible by way of a first removable end cap; a second housing having a second chamber, the second housing having a second axis therethrough; wherein the second chamber is accessible by way of a second removable end cap; wherein the first housing and the second housing are arranged such that the first axis is coaxial with the second axis; wherein the first housing and the second housing are arranged with a gap therebetween capable of receiving a rock sample for ultrasonic evaluation; a sleeve disposed between the first housing and second housing enclosing the gap, wherein the sleeve is capable of enclosing the rock sample; wherein the first chamber comprises a plurality of surface areas defined therein, a first platen defined as the surface area nearest the rock sample, the first platen being perpendicular to the first axis; a first p-wave piezoelectric element mounted on the first platen; a first s-wave piezoelectric element mounted on the first platen adjacent to the first p-wave piezoelectric element; wherein the second chamber comprises a plurality of surface areas defined therein, a second platen defined as the surface area nearest the rock sample, the second platen being perpendicular to the second axis; a second p-wave piezoelectric element mounted on the second platen; a second s-wave piezoelectric element mounted on the second platen adjacent to the second p-wave piezoelectric element; a first channel passing through the first housing arranged to allow pressurized fluid to be supplied through the first channel; a second channel passing through the second housing arranged to allow pressurized fluid to be withdrawn from the second channel; wherein the first channel and the second channel are arranged to allow pressurized fluid to flow through the rock sample in a direction that is substantially parallel to the first and second axis; and wherein each of the piezoelectric elements of the first chamber is arranged substantially opposite to one of the piezoelectric elements of the second chamber.

One example of an ultrasonic evaluation system for evaluating rock specimens comprises: a first housing having a first chamber, wherein the first housing has a first axis therethrough; a second housing having a second chamber, wherein the second housing has a second axis therethrough; wherein the first housing and the second housing are arranged such that the first axis is coaxial with the second axis; wherein the first housing and the second housing are arranged with a gap therebetween; an enclosure disposed between the first housing and second housing enclosing the gap; wherein the first chamber comprises a first platen wherein the first platen is perpendicular to the first axis; a first p-wave piezoelectric element mounted on the first platen; a first s-wave piezoelectric element mounted on the first platen adjacent to the first p-wave piezoelectric element; wherein the second chamber comprises a second platen wherein the second platen is perpendicular to the second axis; a second p-wave piezoelectric element mounted on the second platen; a second s-wave piezoelectric element mounted on the second platen adjacent to the second p-wave piezoelectric element; a first channel passing through the first housing arranged to allow pressurized fluid to be supplied through the first channel; a second channel passing through the second housing arranged to allow pressurized fluid to be withdrawn from the second channel; and wherein the first channel and the second channel are arranged to allow pressurized fluid to flow from the first channel to the second channel in a direction that is substantially parallel to the first and second axis.

One example of a method for ultrasonic evaluation of rock specimens comprises the steps of: (a) providing an ultrasonic evaluation system comprising a first housing having a first chamber, wherein the first housing has a first axis therethrough; a second housing having a second chamber, wherein the second housing has a second axis therethrough; wherein the first housing and the second housing are arranged such that the first axis is coaxial with the second axis; wherein the first housing and the second housing are arranged with a gap therebetween; an enclosure disposed between the first housing and second housing enclosing the gap; wherein the first chamber comprises a first platen wherein the first platen is perpendicular to the first axis; a first p-wave piezoelectric element mounted on the first platen; a first s-wave piezoelectric element mounted on the first platen adjacent to the first p-wave piezoelectric element; wherein the second chamber comprises a second platen wherein the second platen is perpendicular to the second axis; a second p-wave piezoelectric element mounted on the second platen; a second s-wave piezoelectric element mounted on the second platen adjacent to the second p-wave piezoelectric element; a first channel passing through the first housing arranged to a allow pressurized fluid to be supplied through the first channel; and a second channel passing through the second housing arranged to allow the pressurized fluid to be withdrawn from the second channel; and wherein the first channel and the second channel are arranged to allow the pressurized fluid to flow from the first channel to the second channel in a direction that is substantially parallel to the first and second axis; (b) introducing the pressurized fluid to the first channel; (c) withdrawing the pressurized fluid from the first channel; (d) actuating the first s-wave piezoelectric element so as to produce a plurality of first ultrasonic waves passing through the rock specimen; (e) measuring a first response from the first ultrasonic waves with the second s-wave piezoelectric element; (f) actuating the first p-wave piezoelectric element so as to produce a plurality of second ultrasonic waves passing through the rock specimen; and (g) measuring a first response from the second ultrasonic waves with the second p-wave piezoelectric element.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein.

Figure 1:
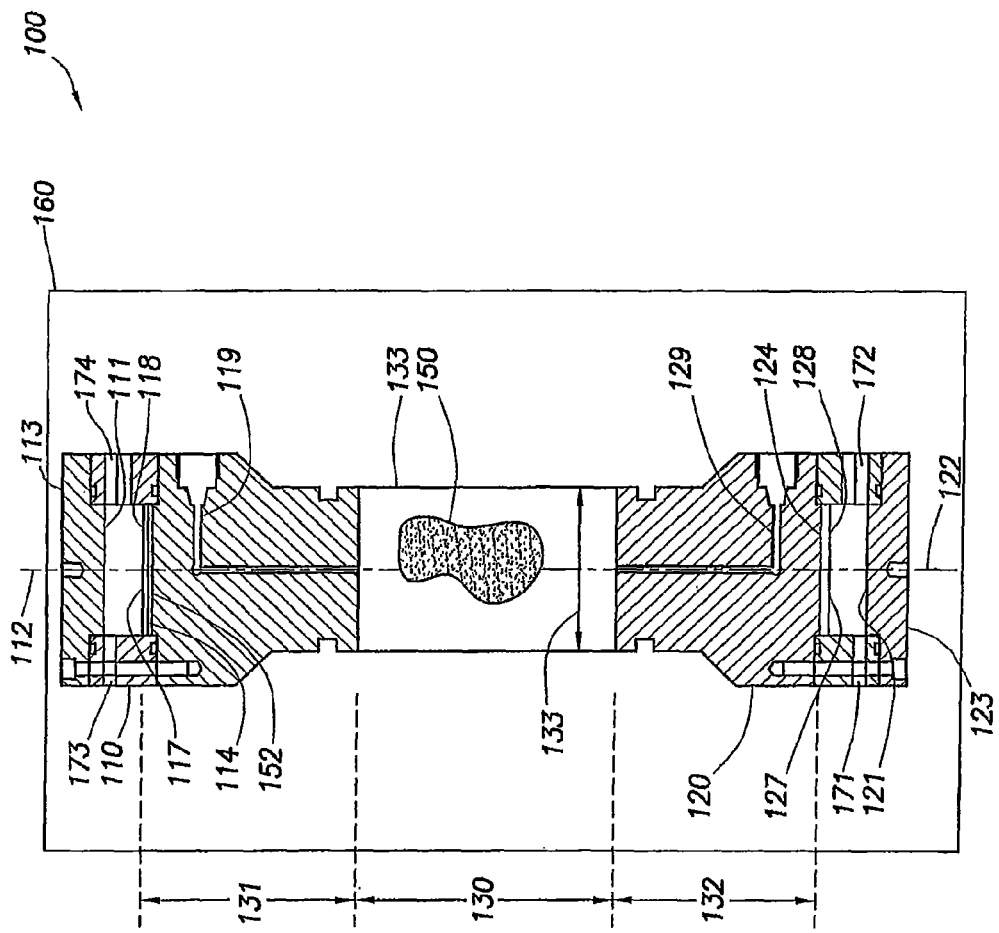
FIG. 1 illustrates an ultrasonic evaluation system in accordance with one embodiment of the present invention.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present invention relates generally to methods and systems for ultrasonic evaluation of test specimens. More particularly, but not by way of limitation, embodiments of the present invention include methods and systems for evaluating rock specimens subjected to high pressures and temperatures by ultrasonic evaluation utilizing various transducer enhancements.

In certain embodiments, ultrasonic evaluation systems are configured to provide more accurate measurements, enhanced protection of transducer elements, fewer metal interfaces between transducer elements and test specimens, and easier access to transducer elements for maintenance and replacement. Additionally, certain embodiments disclosed herein allow for sequential or simultaneous p-wave and s-wave measurements of a test specimen. Ultimately, each of these enhancements translates into a more accurate and efficient ultrasonic evaluation system offering higher resolution measurements.

Reference will now be made in detail to embodiments of the invention, one or more examples of which are illustrated in the accompanying drawings. Each example is provided by way of explanation of the invention, not as a limitation of the invention. It will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations that come within the scope of the invention.

FIG. 1 illustrates an ultrasonic evaluation system in accordance with one embodiment of the present invention.

Ultrasonic evaluation system 100 comprises in part first housing 110 and second housing 120, having gap 130 therebetween capable of receiving test specimen 150 for ultrasonic evaluation. Test specimen may be any material for which ultrasonic evaluation is desired, including, but not limited to, formation rock specimens.

First housing 110 comprises first chamber 111. First chamber 111 in turn includes first platen 114 on which first p-wave piezoelectric element 117 and first s-wave piezoelectric element 118 may be mounted. Piezoelectric elements used in combination with the present invention may comprise any piezoelectric element suitable for inducing ultrasonic waves including, but not limited to, piezoelectric ceramics, quart crystals, piezoelectric ceramics comprising barium titanate, piezoelectric ceramics comprising lead zirconate titanate compositions (often referred to as PZT crystals), piezo-polymers and composites, or any combination thereof. Generally, p-wave piezoelectric elements produce primarily p-waves, whereas s-wave piezoelectric elements produce primarily s-waves.

In certain embodiments, first p-wave piezoelectric element 117 may be mounted adjacent to first s-wave piezoelectric element 118. Mounting each piezoelectric element adjacent one another avoids the undesirable interference errors that result when one piezoelectric element is stacked on top of another.

In some cases, coupling medium 152 may be interposed between first platen 114 and piezoelectric elements 117 and 118 to promote the transfer of sound energy from piezoelectric elements 117 and 118 into and through test specimen 150. Coupling medium 152 may also be useful for removing any air gaps between piezoelectric elements 117 and 118 and first platen 114.

First housing 111 comprises first removable end cap 113 for access to first chamber 111. First removable end cap 113 allows convenient access to first chamber 111 for maintenance and/or replacement of piezoelectric elements 117 and 118.

Second housing 120 comprises elements analogous to first housing 110. More specifically, second housing 120 comprises second chamber 121, second removable end cap 123, second platen 124, second p-wave piezoelectric element 127, and second s-wave piezoelectric element 128.

First platen 114 is arranged directly opposite to second platen 124. More particularly, first housing 110 has first axis 112 running therethrough, whereas, second housing 120 has second axis 122 running through second housing 120. First platen 114 is arranged perpendicular to first axis 112 while second platen 124 is arranged perpendicular to second axis 122. In this way, first and second platens 114 and 124 may be substantially parallel to one another. Additionally, piezoelectric elements 117 and 118 are opposite piezoelectric elements 127 and 128. This arrangement allows first p-wave piezoelectric element 117 to send and receive ultrasonic waves to and from second p-wave piezoelectric element 127. Similarly, this arrangement allows first s-wave piezoelectric element 118 to send and receive ultrasonic waves to and from second s-wave piezoelectric element 118.

First housing 110 may be configured and adapted to minimize metal interfaces between first platen 114 and test specimen 150. Likewise, second housing 120 may be configured and adapted to minimize metal interfaces between second platen 124 and test specimen 150. In this way, ultrasonic interference by extraneous metal interfaces is minimized, producing cleaner ultrasonic transmissions and measurements. In certain embodiments, first housing 110 may be formed as one integral piece to minimize metal interfaces between first platen 114 and test specimen 150. Likewise, second housing 120 may be formed as one integral piece to minimize metal interfaces between second platen 124 and test specimen 150.

In certain embodiments, the distance between first platen 114 and piezoelectric elements 117 and 118 is minimized to avoid signal degradation between piezoelectric elements 117 and 118 and first platen 114. In certain embodiments, the distance between first platen 114 and piezoelectric elements 117 and 118 is limited to no more than about 3 inches. In other embodiments, the distance between first platen 114 and piezoelectric elements 117 and 118 is limited to no more than about 1.5 $L_1/D$, where $L_1$ is the distance between first platen 114 and piezoelectric elements 117 and 118, where D is the transverse distance 133 across gap 130. Similarly, in certain embodiments, the distance between second platen 124 and piezoelectric elements 127 and 128 is limited to no more than about 3 inches. In other embodiments, the distance between second platen 124 and piezoelectric elements 127 and 128 is limited to no more than about 1.5 $L_2/D$, where $L_2$ is the distance between second platen 124 and piezoelectric elements 127 and 128 where D is again the transverse distance 133 across gap 130.

Gap 130 is provided between first housing 110 and second housing 120 for receiving test specimen 150. Test specimen 150 may be any material for which ultrasonic evaluation is desired, including, but not limited to, formation rock samples. Enclosure 133 encloses test specimen 150 in gap 130. In certain embodiments, enclosure 133 may be a sleeve, as shown here in FIG. 1.

First channel 119 and second channel 129 allow for the introduction and withdrawal of fluid to and from test specimen 150 within enclosure 133. Fluid flow may be established during testing as desired. In this way, the systems and methods herein contemplate ultrasonic measurements while fluid flow is established through test specimen 150.

In certain embodiments, enclosure 133 is sealed with respect to first housing 110 and second housing 120 to allow the region of gap 130 to be pressurized. Accordingly, with pressurized and/or heated fluid may be directed through test specimen 150. In other embodiments, enclosure 133 is not sealed, but instead simply directs fluid flow preferentially from first channel 119 through test specimen 150 to second channel 129 or vice versa. Where enclosure 133 is not sealed, optional outer pressure chamber 160 may be provided to allow pressurization of the entire system as opposed to limiting pressurization to the localized sealed region of enclosure 133.

Channels 171 and 172 shown here in second housing 120 may be provided to allow for the flow of a cooling fluid. The cooling fluid may be provided at a flow rate that maintains a desired temperature and pressure of the piezoelectric elements 127 and 128. Optional analogous channels 173 and 174 are shown on first housing 110, which also function to allow for the flow of cooling fluid if desired.

Certain embodiments of ultrasonic evaluation system 100 are adapted to operate at frequencies from about from about 0.5 MHz to about 1 MHz, 0.1 MHz to about 2.25 MHz, at frequencies from about 15 MHz to about 25 MHz, and at frequencies up to about 150 MHz.

Figure 2C:
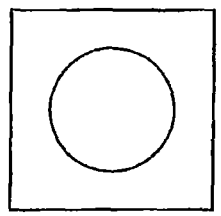
FIGS. 2A-2C illustrates an ultrasonic evaluation system in accordance with an alternate embodiment of the present invention.
Figure 2B:
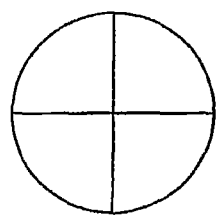
Figure 2A:
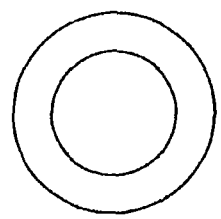

Other physical configurations of the piezoelectric elements are possible. These alternate physical configurations result in other arrangements of p-wave and s-wave propagations and polarization directions. By way of illustration of other various geometric shapes that are possible, FIG. 2 shows alternate physical configurations of various p-wave and s-wave transducers and crystals. In particular, FIG. 2A shows a doughnut configuration; FIG. 2B shows alternating quarter-circles; and FIG. 2C shows a circular element circumscribed by a square element. Each of these elements may be arranged with respect to one another in a coplanar fashion or in a stacked configuration.

Where more than one pair of transducers is used, it is recognized that one pair may operate at a first frequency or range of frequencies, whereas the second pair operates at a second frequency or range of frequencies.

It is explicitly recognized that any of the elements and features of each of the devices described herein are capable of use with any of the other devices described herein with no limitation, including any features or embodiments described in the background. Furthermore, it is explicitly recognized that the steps of the methods herein may be performed in any order except unless explicitly stated otherwise or inherently required otherwise by the particular method.

To facilitate a better understanding of the present invention, the following examples of certain embodiments are given. In no way should the following examples be read to limit, or define, the scope of the invention.

EXAMPLE

The following experiment demonstrates the efficacy of certain embodiments of the present invention. In one experiment, a rock sample was compacted in a pressure chamber. This compaction experiment, described below, was intended to extract the native oil-rich minerals from the rock sample, by using elevated temperature and steam.

An ultrasonic transducer assembly (described in FIG. 1) was used to collect and record the waveforms of ultrasonic energy in which the rock was compacted and the water was injected. The change in the character of the waveforms is due to the change in pore fluid saturation, fluid viscosity, rock stress, and temperature.

In this experiment, a 1-inch diameter cylindrical specimen of rock containing bitumen-rich minerals with a low-viscosity (called heavy-oils), was assembled with the transducers as described in FIG. 1.

The entire assembly of transducers and specimen was then enclosed in a pressure chamber, a standard chamber commonly used in rock mechanical laboratories, where the chamber is equipped with ports for the electrical wires for the ultrasonic transducers and ports for the pipes to conduct pore fluids to and from the rock specimen. The pressure chamber was filled with mineral oil referred to as a confining fluid. While maintaining a confining fluid pressure of 450 psig, the fluids in the rock's pore spaces was allowed to drain into a tank where the pore fluid pressure was kept below 50 psi.

The confining fluid was heated, starting at a room temperature of up to 260 degrees Fahrenheit (F) using electrical heaters embedded inside the pressure chamber. Ultrasonic waveforms were gathered and recorded as the temperature was being increased. The waveform labeled in FIG. 3 as #1 was recorded, with a chamber confining pressure of 450 psig and a chamber temperature of 260 degrees F. The chamber temperature was then increased to 390 degrees F. and a chamber pressure of 450 psig. The recorded waveform is labeled #9 in FIG. 3.

The pressure of the confining fluid was then kept constant at 450 psig, and the temperature was held to 300 degrees F. The rock specimen was injected with distilled water, allowing the original fluids in the rock to flow into a collection tank or cell. Water was then injected through the rock sample, at a pore fluid pressure of 100 psig, displacing the oily bitumen minerals into a collection cell. Waveforms from the compressional and shear wave transducers were collected every 10 minutes. Data collection stopped after injecting 50 cc of water through the rock specimen. The temperature was allowed to cool down to room temperature. The confining fluid pressure was reduced to 0 psig, at which point the experiment was stopped.

Figure 3:
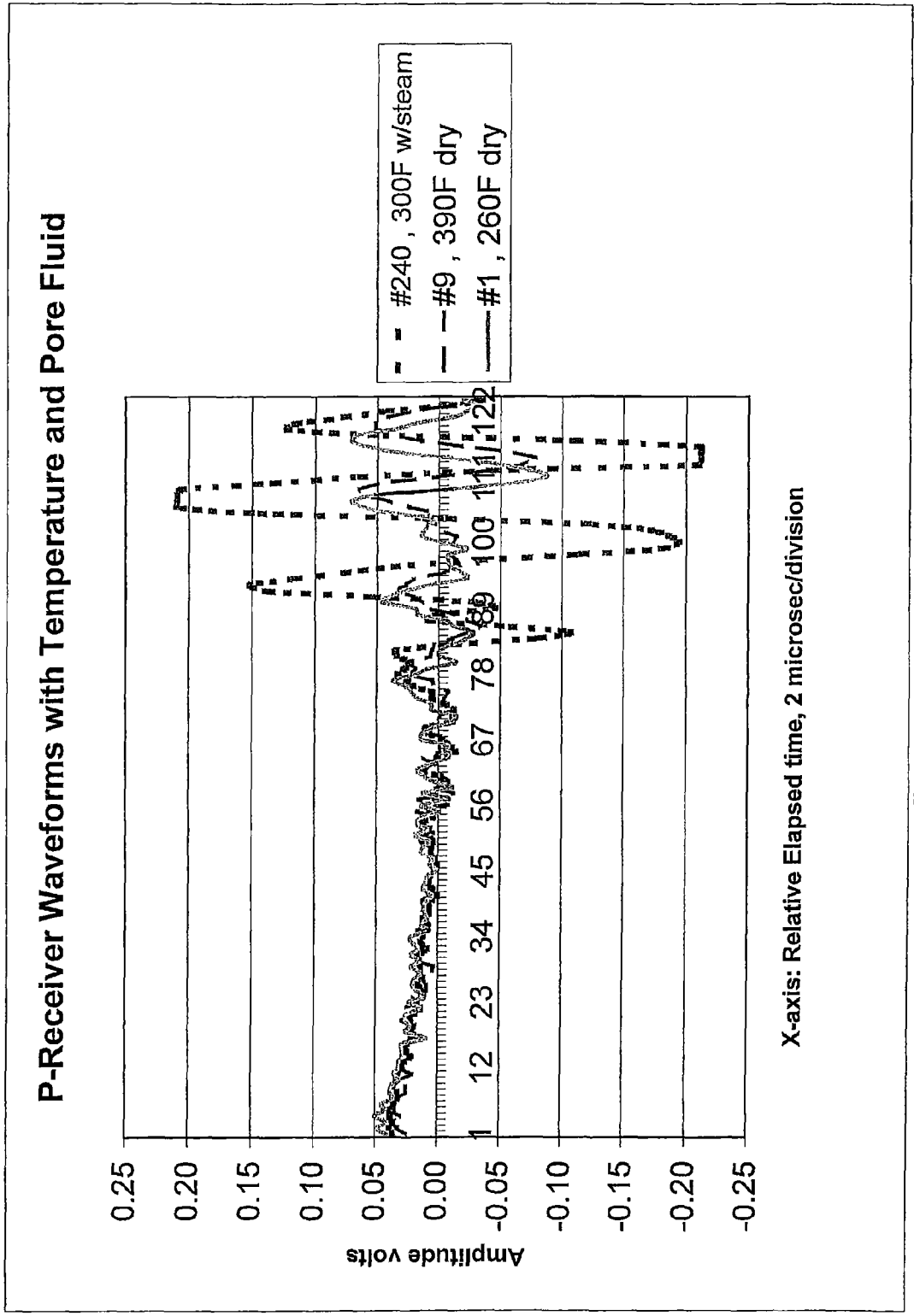
FIG. 3 shows ultrasonic waveforms gathered at different temperatures while an oil-rich rock specimen was heated from a compaction test on a shale-rich rock sample containing bitumen.

Thus, FIG. 3 shows ultrasonic waveforms gathered at different temperatures while an oil-rich rock specimen was heated to 390 degrees Fahrenheit from a compaction test on a shale-rich rock sample that contains some bitumen. These are segments of the waves recorded by an oscilloscope attached to the compression (P) pair of transmitter and receiver crystals. More specifically, FIG. 3 shows three ultrasonic waveforms from the compressional (P) receiver while the rock samples are at the confining pressure of 450 psig.

A large increase in amplitude is observed when the rock gets saturated with brine at 100 psig, but there is no significant change in ultrasonic velocity. Due to the high temperature of 300 degrees F., the injected water turned into steam and improved the contact in the interface between the metal and the rock, resulting in an increase in amplitude of the waveform labeled in FIG. 3 as #240. The change in the character of the waveforms was due to the change in pore fluid saturation, fluid viscosity, rock stress, and temperature.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations and equivalents are considered within the scope and spirit of the present invention.

What is claimed is:

1. A system for evaluating a rock specimen by ultrasonic evaluation comprising:
   a first housing having a first chamber, the first housing having a first axis therethrough;
   wherein the first chamber is accessible by way of a first removable end cap;
   a second housing having a second chamber, the second housing having a second axis therethrough;
   wherein the second chamber is accessible by way of a second removable end cap;
   wherein the first housing and the second housing are arranged such that the first axis is coaxial with the second axis;
   wherein the first housing and the second housing are arranged with a gap therebetween configure to receive a rock sample for ultrasonic evaluation;
   a sleeve disposed between the first housing and second housing enclosing the gap, wherein the sleeve is configure to enclose the rock sample;
   wherein the first chamber comprises a plurality of surface areas defined therein, a first platen defined as the surface area nearest the rock sample, the first platen being perpendicular to the first axis;
   a first p-wave piezoelectric element mounted on the first platen;
   a first s-wave piezoelectric element mounted on the first platen adjacent to the first p-wave piezoelectric element;
   wherein the second chamber comprises a plurality of surface areas defined therein, a second platen defined as the surface area nearest the rock sample, the second platen being perpendicular to the second axis;
   a second p-wave piezoelectric element mounted on the second platen;
   a second s-wave piezoelectric element mounted on the second platen adjacent to the second p-wave piezoelectric element;
   a first channel passing through the first housing arranged to allow pressurized fluid to be supplied through the first channel;
   a second channel passing through the second housing arranged to allow pressurized fluid to be withdrawn from the second channel;
   wherein the first channel and the second channel are arranged to allow pressurized fluid to flow through the rock sample in a direction that is substantially parallel to the first and second axis; and wherein each of the piezoelectric elements of the first chamber is arranged substantially opposite to one of the piezoelectric elements of the second chamber.

2. The system of claim 1 wherein the first p-wave piezoelectric element is directly opposite of the second p-wave piezoelectric element and wherein the first s-wave piezoelectric element is directly opposite of the second s-wave piezoelectric element.

3. An ultrasonic evaluation system for evaluating rock specimens comprising:

a first housing having a first chamber, wherein the first housing has a first axis therethrough;

a second housing having a second chamber, wherein the second housing has a second axis therethrough;

wherein the first housing and the second housing are arranged such that the first axis is coaxial with the second axis;

wherein the first housing and the second housing are arranged with a gap therebetween;

an enclosure disposed between the first housing and second housing enclosing the gap;

wherein the first chamber comprises a first platen wherein the first platen is perpendicular to the first axis;

a first p-wave piezoelectric element mounted on the first platen;

a first s-wave piezoelectric element mounted on the first platen adjacent to the first p-wave piezoelectric element;

wherein the second chamber comprises a second platen wherein the second platen is perpendicular to the second axis;

a second p-wave piezoelectric element mounted on the second platen;

a second s-wave piezoelectric element mounted on the second platen adjacent to the second p-wave piezoelectric element;

a first channel passing through the first housing arranged to allow pressurized fluid to be supplied through the first channel;

a second channel passing through the second housing arranged to allow pressurized fluid to be withdrawn from the second channel; and wherein the first channel and the second channel are arranged to allow pressurized fluid to flow from the first channel to the second channel in a direction that is substantially parallel to the first and second axis.

4. The ultrasonic evaluation system of claim 3 wherein the second housing is one integral unit and wherein no other metal structures are interposed between the second housing and the gap.

5. The ultrasonic evaluation system of claim 4 wherein the first housing is one integral unit and wherein no other metal structures are interposed between the first housing and the gap.

6. The ultrasonic evaluation system of claim 3 wherein the first housing and the second housing are one integral unit.

7. The ultrasonic evaluation system of claim 4 wherein the first p-wave piezoelectric element and the first s-wave piezoelectric element are each flat, coplanar, and shaped in the form of a semicircle.

8. The ultrasonic evaluation system of claim 7 wherein the second p-wave piezoelectric element and the second s-wave piezoelectric element are each flat, coplanar, and shaped in the form of a semicircle.

9. The ultrasonic evaluation system of claim 4 wherein the first p-wave piezoelectric element and the first s-wave piezoelectric element are each flat and wherein one of the first p-wave piezoelectric element and the first s-wave piezoelectric element is shaped in the form of a quarter-circle, a circular segment, or a square.

10. The ultrasonic evaluation system of claim 4 wherein the first p-wave piezoelectric element and the first s-wave piezoelectric element are each flat and wherein one of the p-wave piezoelectric element and the first s-wave piezoelectric element forms an annular ring around the other.

11. The ultrasonic evaluation system of claim 4 wherein the first p-wave piezoelectric element and the first s-wave piezoelectric element are both mounted directly on the first platen.

12. The ultrasonic evaluation system of claim 4 wherein the first p-wave piezoelectric element and the first s-wave piezoelectric element are both mounted on the first platen by way of an epoxy that secures each piezoelectric element to the first platen.

13. The ultrasonic evaluation system of claim 4 wherein a first coupling medium is interposed between the first p-wave piezoelectric element and the first platen and wherein a second coupling medium is interposed between the first s-wave piezoelectric element and the first platen, wherein the coupling medium is a conductive gel wherein the first coupling medium and the second coupling medium comprise the same conductive gel.

14. The ultrasonic evaluation system of claim 4 wherein the first chamber is accessible by way of a first removable end cap and wherein second chamber is accessible by way of a second removable end cap.

15. The ultrasonic evaluation system of claim 4 wherein the enclosure is a sleeve that preferentially directs fluid flow parallel to the first axis and the second axis.

16. The ultrasonic evaluation system of claim 3 wherein a first distance extends from the first platen to the gap, wherein a transverse distance extends across the enclosure, wherein the transverse distance is a largest distance across the enclosure that extends transversely to the first axis, and wherein a first ratio of the first distance to the transverse distance is no more than about 1.5.

17. The ultrasonic evaluation system of claim 16 wherein a second distance extends from the second platen to the gap and wherein a second ratio of the second distance to the transverse distance is no more than about 1.5.

18. The ultrasonic evaluation system of claim 4 further comprising an outer pressure chamber that encloses the first housing, the second housing, and the gap to provide an enclosed space that may be pressurized with fluid.

19. The ultrasonic evaluation system of claim 4 wherein the first p-wave piezoelectric element and the first s-wave piezoelectric element are adapted to operate at frequencies from about 0.1 MHz to about 1 MHz.

20. The ultrasonic evaluation system of claim 4 wherein the first p-wave piezoelectric element and the first s-wave piezoelectric element are adapted to operate at frequencies from about 15 MHz to about 25 MHz.

21. The ultrasonic evaluation system of claim 4 wherein the first p-wave piezoelectric element and the first s-wave piezoelectric element are adapted to operate at frequencies up to about 150 MHz.

22. The ultrasonic evaluation system of claim 4 wherein the first p-wave piezoelectric element and the first s-wave piezoelectric element are adapted to operate at a first frequency and wherein the second p-wave piezoelectric element and second first s-wave piezoelectric element are adapted to operate at a second frequency, wherein the first frequency is different than the second frequency.

23. The ultrasonic evaluation system of claim 3 further comprising a third channel and a fourth channel wherein the third channel and the fourth channel are arranged to provide flow of a coolant to and from the first housing.

24. A method for ultrasonic evaluation of rock specimens comprising the steps of:
(a) providing an ultrasonic evaluation system comprising a first housing having a first chamber, wherein the first housing has a first axis therethrough; a second housing having a second chamber, wherein the second housing has a second axis therethrough; wherein the first housing and the second housing are arranged such that the first axis is coaxial with the second axis; wherein the first housing and the second housing are arranged with a gap therebetween; an enclosure disposed between the first housing and second housing enclosing the gap; wherein the first chamber comprises a first platen wherein the first platen is perpendicular to the first axis; a first p-wave piezoelectric element mounted on the first platen; a first s-wave piezoelectric element mounted on the first platen adjacent to the first p-wave piezoelectric element; wherein the second chamber comprises a second platen wherein the second platen is perpendicular to the second axis; a second p-wave piezoelectric element mounted on the second platen; a second s-wave piezoelectric element mounted on the second platen adjacent to the second p-wave piezoelectric element; a first channel passing through the first housing arranged to a allow pressurized fluid to be supplied through the first channel; and a second channel passing through the second housing arranged to allow the pressurized fluid to be withdrawn from the second channel; and wherein the first channel and the second channel are arranged to allow the pressurized fluid to flow from the first channel to the second channel in a direction that is substantially parallel to the first and second axis;
(b) introducing the pressurized fluid to the first channel;
(c) withdrawing the pressurized fluid from the first channel;
(d) actuating the first s-wave piezoelectric element so as to produce a plurality of first ultrasonic waves passing through the rock specimen;
(e) measuring a first response from the first ultrasonic waves with the second s-wave piezoelectric element;
(f) actuating the first p-wave piezoelectric element so as to produce a plurality of second ultrasonic waves passing through the rock specimen; and
(g) measuring a first response from the second ultrasonic waves with the second p-wave piezoelectric element.

25. The method of claim 24 wherein steps (d)-(g) are performed simultaneously with steps (b) and (c).

* * * * *